United States Patent

Valbert

[11] Patent Number: 6,060,627
[45] Date of Patent: May 9, 2000

[54] POLYOL PURIFICATION

[75] Inventor: Jon R. Valbert, Arlington, Mass.

[73] Assignee: Arco Chemical Technology, L.P., Greenville, Del.

[21] Appl. No.: 09/074,504

[22] Filed: May 8, 1997

[51] Int. Cl.[7] ............................ C07C 31/18; C07C 27/26

[52] U.S. Cl. ........................ 568/852; 536/167; 536/168; 536/149; 536/2; 554/18.6; 568/869

[58] Field of Search ..................... 554/168, 167, 554/2, 149; 536/18.6; 568/852, 869

[56] References Cited

U.S. PATENT DOCUMENTS

| | | | |
|---|---|---|---|
| 4,983,329 | 1/1991 | Cooper | 260/410.7 |
| 5,571,935 | 11/1996 | Sekula et al. | 554/168 |
| 5,681,939 | 10/1997 | Ferenz | 536/18.6 |

*Primary Examiner*—James O. Wilson
*Assistant Examiner*—Howard Owens
*Attorney, Agent, or Firm*—William C. Long

[57] ABSTRACT

A water and allylic compound containing propoxylated glycerin stream is reduced in water content by evaporation and flashed at reduced pressure and elevated temperature to reduce the water content to 1000 ppm or less, and thereafter stripping allylic impurities from the propyxylated glycerin.

3 Claims, 1 Drawing Sheet

POLYOL PURIFICATION

BACKGROUND OF THE INVENTION

1. Field of the Invention

The present invention relates to the separation of impurities from polyols such as propoxylated glycerin by a procedure whereby the water content of the polyols is reduced by evaporation, to a modest level, and subsequently the resulting mixture is flashed to reduce the water content to 1000 ppm or lower and light organic impurities are thereafter stripped from the polyol.

2. Description of the Prior Art

Fatty acid—esterified propoxylated glycerins have been proposed for use as reduced caloric fat substitutes in food products. See, for example, U.S. Pat. No. 4,861,613.

These materials are conveniently prepared by esterification of propoxylated glycerin as described, for example, in U.S. Pat. Nos. 5,681,939 and 4,983,329.

The polyol which is employed in such esterification reactions should be free of contaminants which would adversely affect the ultimate use of the esterified propoxylated polyol, such impurities including allylic materials such as allyl alcohol and other allylic compounds such as allyl alcohol ethers which are lower boiling that the polyol.

The present invention provides a process for the efficient separation of low boiling allylic impurities from propoxylated glycerin polyol.

Propoxylated glycerin polyol, as generally produced, contains substantial amounts of water and low boiling allylic impurities. Problems are encountered when attempts are made to strip low-boiling allylic materials from polyols which contain substantial amount of water.

BRIEF DESCRIPTION OF THE INVENTION

In accordance with the present invention, propoxylated glycerin polyol containing substantial amounts of water and also containing low boiling allylics such as allyl alcohol and ethers of allyl alcohol and propylene glycol, is first heated and the water contained therein evaporated overhead until the water content is reduced to a level which is conveniently achievable by conventional evaporation eg. 2 wt % or less, preferably 1.5 wt % or less. Some allyl alcohol is removed during the evaporation. The resulting mixture is then flashed at elevated temperature and reduced pressure in the upper section of an appropriate stripper whereby the water content of the non-flashed liquid is further reduced to 1000 ppm by weight or less. Thereafter, the polyol is stripped at conditions of reduced pressure and remaining allylic materials are removed as overhead vapor leaving a polyol bottoms which is essentially free of contained allylic materials.

DESCRIPTION OF THE DRAWING

The accompanying drawing illustrates in schematic form a practice of the invention.

DETAILED DESCRIPTION

Figure 1:
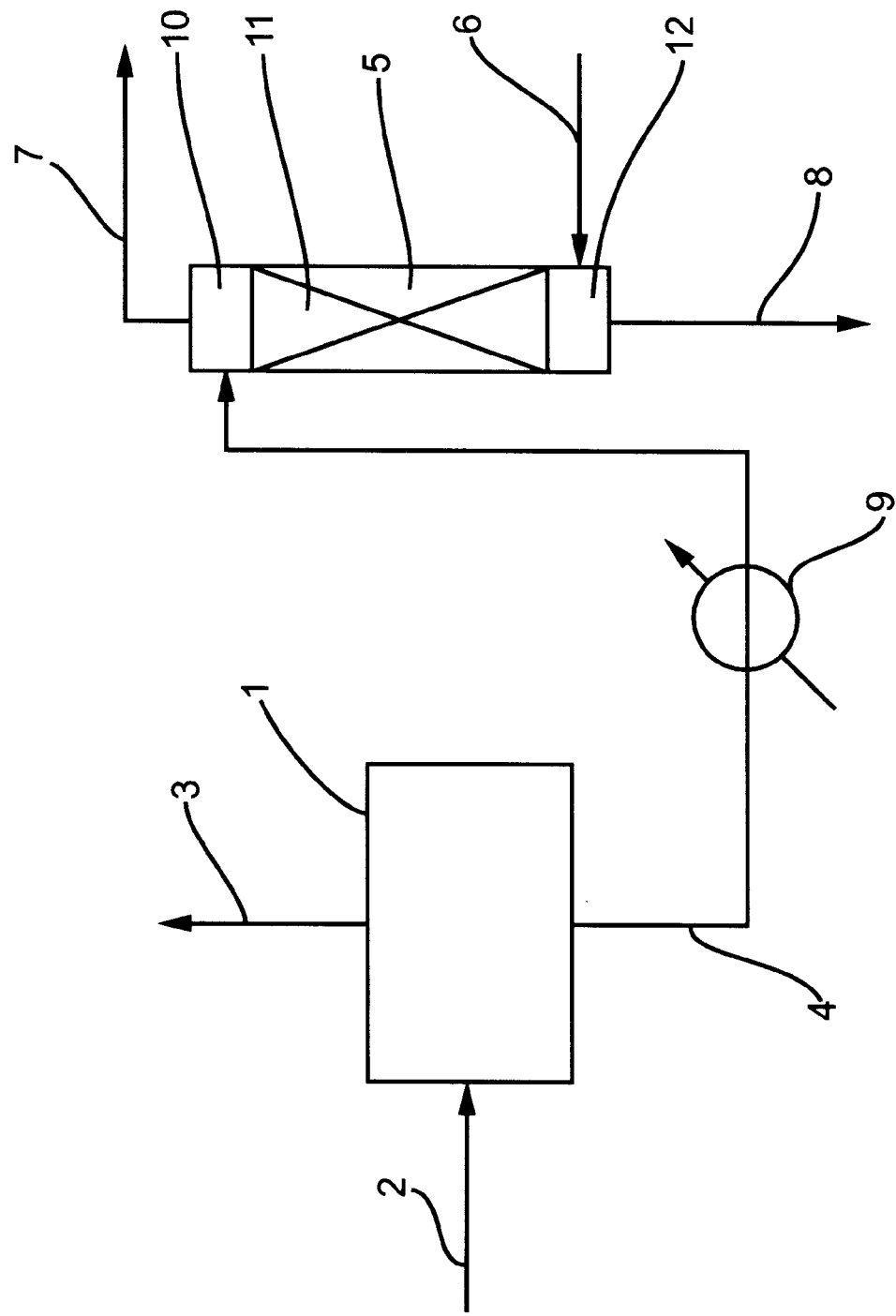

The polyol employed in the process of this invention may be prepared by any of the standard methods known in the art such as, for example, the base-catalyzed reaction of propylene oxide with glycerin. While the molar ratio of propylene oxide to glycerin is not critical, if the esterified propoxylated glycerin is to be used as a reduced calorie fat substitute it is preferred that from 2 to 20 moles of epoxide be reacted per mole of glycerin. The propoxylation of glycerin can be carried out by the addition of propylene oxide to glycerin in the presence of a catalytic amount of an alkali metal alkoxylate at a temperature of from about 70° C. to 130° C. The alkali metal alkoxylate is desirably prepared by heating an alkali metal compound such as sodium hydroxide or potassium hydroxide with glycerin at an elevated temperature while continuously removing water, preferably under reduced pressure. Preferably, sufficient catalyst is present during propoxylation to provide an alkali metal content of about 0.0003 moles to 3.3 moles alkali metal per 100 g of glycerin. The propylene oxide is preferably fed incrementally into a reactor containing the glycerin and catalyst at a rate sufficient to maintain a pressure within the reactor of about 40 to 80 psi. The degree of propoxylation is controlled, and thus the molecular weight of the propoxylated glycerin as well, by regulating the amount of propylene oxide fed to the reactor. After the desired molecular weight is reached, the alkali metal may be removed prior to esterification by any suitable method such as adsorption, ion exchange, or extraction.

The propoxylated glycerin thus obtained will have a chemical structure generally as follows:

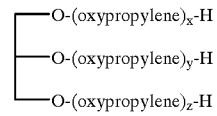

wherein x, y and z are the same or different and are 0 or preferably an integer of from 1 to 20 with the sum of x+y+z preferably ranging from 2 to 20 (more preferably, 3 to 15). The oxypropylene units in the propoxylated glycerin have the structure

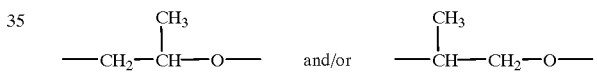

with the former type of structure preferably predominating.

These polyol products contain various allylic components in addition to the propoxylated glycerin. Specifically, the polyol products contain allyl alcohol and mono-and di-ethers of allyl alcohol and propylene glycol which are formed during the preparation procedure.

The polyol product from the propoxylation is advantageously contacted with ion exchange resin in order to remove the alkali metal values used to catalyze the polyol formation in accordance with known procedures. Water, illustratively in amount of up to 5 wt % is added to the polyol to facilitate ion exchange treatment.

Such procedures are described, for example, in U.S. Pat. Nos. 5,254,227 and 4,985,551 the disclosures of which are incorporated herein by reference.

By these prior procedures there is produced a propoxylated glycerin polyol mixture containing both water and allylic materials and it is this polyol mixture which is purified in accordance with this invention. Referring to the attached drawing, the polyol mixture is introduced into evaporation zone 1 via line 2. In zone 1 the polyol is heated and water and some allyl alcohol is evaporated and removed via line 3. Preferably the evaporation is at about atmospheric pressure and elevated temperature and is continued to the extent sufficient to reduce the water content to 2 wt % or lower. This overhead stream can be condensed and further treated (not shown).

The bottoms polyol stream now containing 2 wt % or less of water preferably 1.5 wt % or less passes via line 4 to the upper flashing section 10 of stripper 5. The bottoms stream from evaporator 1 is preferably further heated in supplemental heater 9 to a suitable elevated temperature of 160–165° C. before introduction into stripper 5. Upon introduction into the upper section 10 of stripper 5 components of the hot stream from evaporator 1 are flashed at reduced pressure, eg. 20 mm Hg to reduce the water content of the liquid to 1000 ppm by weight or less. During this flash the temperature is reduced to 130–145° C. Liquid then passes downwardly through zone 11 which is a conventional packed stripper and allylic impurities are stripped therefrom using stripping gas such as steam or nitrogen introduced via line 6 to zone 12 below the packing. The allylic values contained in the feed stream are removed overhead along with stripping gas via line 7. A bottoms polyol stream essentially free of allylic materials is recovered via line 8 and this stream can be esterified with fatty acids by known procedures to form esterified propoxylated glycerin suitable for use in food products.

In accordance with the present invention, the water content of the polyol is first reduced as far as practical by evaporation, e.g. to 2.0 wt % or less, preferably 1.5 wt % or less. The liquid from the evaporator at about 160–165° C. is flashed to a temperature of 130–145° C. at low pressure in the upper section of the flash zone to reduce the water content of the liquid to 1000 ppm or less. At the resulting low water content, the allylic impurities in the polyol stream can be stripped successfully from the liquid polyol. Where higher amounts of water are contained in the polyol stream, insufficient vapor pressure of the allylic impurities can be developed to insure their removal.

The following example illustrates the invention:

A stream of 9586.9 lbs/hr of glycerin propoxylated with 5 mols of propylene oxide containing 5 wt % water, 0.1% allyl alcohol and 0.08% propylene glycol allyl ethers is fed via line 2 to reboiler evaporator 1. The reboiler evaporator is heated to 160° C. with medium pressure steam and of the 477.9 lbs/hr water contained in the feed to this unit, 386.2 lbs are vaporized and removed via line 3 along with some allyl alcohol. Liquid from the reboiler comprises about 91.7 lb/hr water along with the propoxylated glycerine and this stream is removed via line 4 and heated to 165° C. in exchanger 9 with medium pressure steam. The heated stream is flashed into the top of the stripper 5 to 20 mm Hg absolute pressure, whereby 82.7 lb/hr water vaporizes and the liquid phase cools to 145° C. having a residual 9.0 lb/hr water in the liquid phase, ie. 940 ppm (wt). The stripper is a 1' diameter 316 stainless steel column containing 8' of structured 316 stainless steel packing. Into the bottom is introduced 275.4 lbs/hr medium pressure stripping steam via line 6. The bottoms from the stripper is found to have no detectable allyl alcohol and 0.4 lb/hr (44 ppm wt) of propylene glycol allyl ethers and is removed via line 8. The overhead flow of 366.2 lb/hr contains some of the allyl alcohol and the bulk of the propylene glycol allyl ethers and is removed via line 7.

I claim:

1. In a process for the separation of allylic materials from a propoxylated glycerin product stream also containing water, the improvement which comprises heating the said product stream and evaporating water overhead at atmospheric or higher pressure from the propoxylated glycerin product stream to reduce the water content to 2.5 wt % or less, and flashing the liquid stream from the evaporation at elevated temperature and 5 to 20 mm Hg absolute pressure to further reduce the water content to 1000 ppm or less, and stripping allylic materials from the flashed liquid.

2. The process of claim 1 wherein water is evaporated from the propoxylated glycerin stream to 1.5 wt % or less.

3. The process of claim 1 wherein steam or nitrogen is used to strip allylic materials from the flashed liquid.

* * * * *